United States Patent [19]
Dschida

[11] Patent Number: 6,059,446
[45] Date of Patent: May 9, 2000

[54] APPARATUS FOR MIXING THE CONTENTS OF MICROCENTRIFUGE TUBES

[76] Inventor: William J. A. Dschida, 1807 Columbus Ave., McKinleyville, Calif. 95519

[21] Appl. No.: 09/081,742

[22] Filed: May 19, 1998

Related U.S. Application Data

[60] Provisional application No. 60/074,595, Feb. 12, 1998.

[51] Int. Cl.[7] .................................................. B01F 11/00
[52] U.S. Cl. .......................................... 366/215; 366/208
[58] Field of Search ................................. 366/144, 145, 366/208, 209, 210, 212, 214, 215, 219, 239, 240

[56] References Cited

U.S. PATENT DOCUMENTS

| | | |
|---|---|---|
| 3,159,384 | 12/1964 | Davis . |
| 3,184,222 | 5/1965 | Aronowitz et al. ...................... 366/209 |
| 3,347,531 | 10/1967 | Strong et al. ............................. 366/145 |
| 3,401,034 | 9/1968 | Moore . |
| 3,850,580 | 11/1974 | Moore et al. . |
| 3,975,001 | 8/1976 | Moore et al. ............................ 366/111 |
| 4,004,883 | 1/1977 | Meyer et al. . |
| 4,057,148 | 11/1977 | Meyer et al. . |
| 4,118,801 | 10/1978 | Kraft et al. .............................. 366/208 |
| 4,202,634 | 5/1980 | Kraft et al. .............................. 366/208 |
| 4,305,668 | 12/1981 | Bilbrey .................................... 366/208 |
| 4,677,843 | 7/1987 | Schroeder ............................... 366/145 |
| 4,747,693 | 5/1988 | Kahl ........................................ 366/208 |
| 4,848,917 | 7/1989 | Benin et al. ............................. 366/208 |
| 4,895,453 | 1/1990 | Devlin et al. ........................... 366/219 |
| 5,215,376 | 6/1993 | Schulte et al. .......................... 366/348 |
| 5,577,837 | 11/1996 | Martin et al. ........................... 366/145 |

FOREIGN PATENT DOCUMENTS

| | | | |
|---|---|---|---|
| 1 409 780 | 7/1965 | France | .................................... 366/210 |
| 1 699 574 | 12/1991 | U.S.S.R. | ................................. 366/209 |

*Primary Examiner*—Tony G. Soohoo
*Attorney, Agent, or Firm*—Barbara J. Luther

[57] ABSTRACT

The present invention reveals an apparatus for mechanically finger vortexing microcentrifuge tubes. The apparatus is made of a box; a tube-holding rack having a frame, where the top of a microcentrifuge tube is held in a pivotal position; a base plate having a plurality of upright ribs, where the ribs cause a pull-and-release action either directly or indirectly on a microcentrifuge tube; a wheel, where the wheel is connected to an armature and where the armature is connected to the base plate; and a motor with a shaft, where the shaft is connected to the wheel. In the operation of the apparatus, the motor and the shaft impart a circular motion to the wheel and the armature transposes the circular motion of the motor-wheel to a reciprocating motion on the base plate. The reciprocating motion of the base plate causes the ribs to mix the contents of the microcentrifuge tubes.

13 Claims, 6 Drawing Sheets

APPARATUS FOR MIXING THE CONTENTS OF MICROCENTRIFUGE TUBES

This application claims the benefit of U.S. Provisional Application Ser. No. 60/074,595, filed Feb. 12, 1998, the entire contents of which are hereby incorporated by reference and relied upon.

BACKGROUND OF THE INVENTION

1. Field of the Invention

The present invention is a device for resuspending liquid contents of microcentrifuge tubes by simulating the technique of finger vortexing.

Since the advent of culturing microorganisms, technology has been developed to mix liquid suspensions in a controlled and rhythmic pattern. Circular shakers continuously swirl samples in a circular motion, while reciprocating shakers mix samples with a back and forth motion. Motor-driven propellers, as well as forced aeration, serve to mix samples by homogenizing the contents with direct physical agitation.

A similar technology has been developed for mixing smaller sample volumes, e.g., 0.5–1.5 ml microcentrifuge tubes typically used for overnight bacterial plasmid preparations. The technology is simply a miniaturized version of the larger capacity shakers; the same basic circular motion used to mix large volume samples is used to mix small volume samples. These devises are maladapted to mixing small volumes of cells and solutions used in molecular and chemical analyses.

Figure 1:
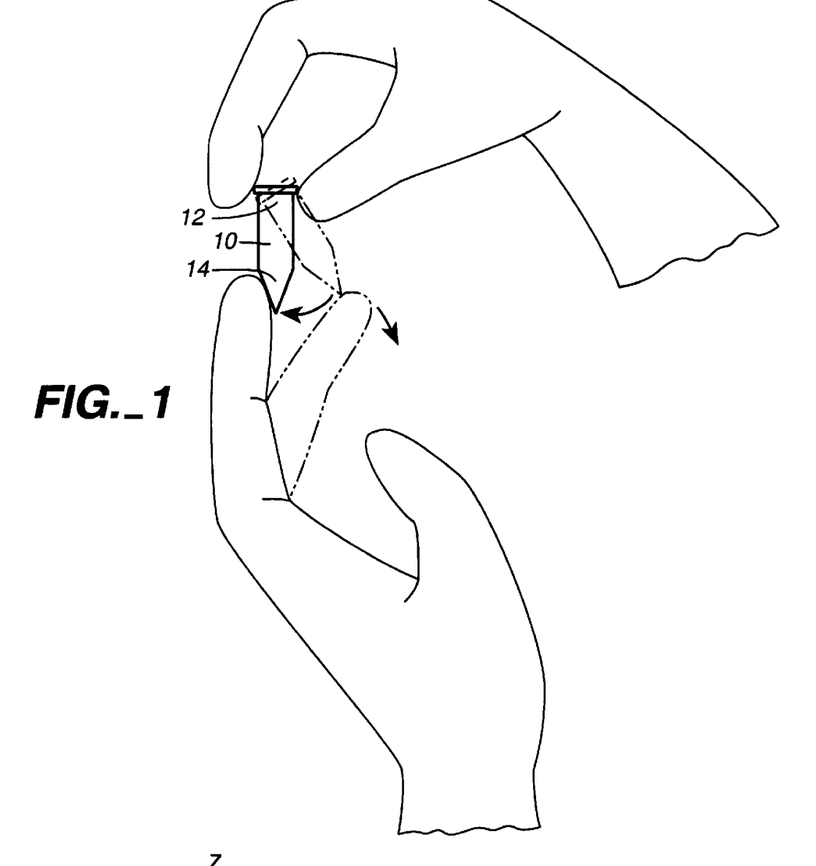
Figure 2A:
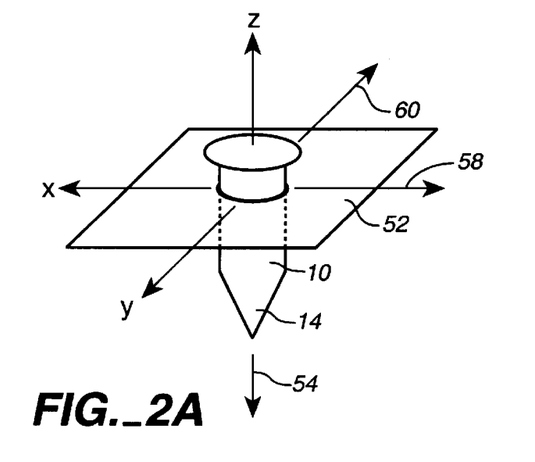
FIGS. 2A and 2B show the finger vortexing principle as applied to microcentrifuge tube mixing in a three dimensional model with the present invention, the tube-holding rack 20 lies in the x-y plane 52, and the tube 10 in its original, resting position lies along a vertical z-axis 54. The base 24 moves in the direction of the x-axis 58, pulling-and-releasing the tube bottom 14 along the x-z plane 56. The tube top or neck 12 pivots on the y-axis 60.
Figure 2B:
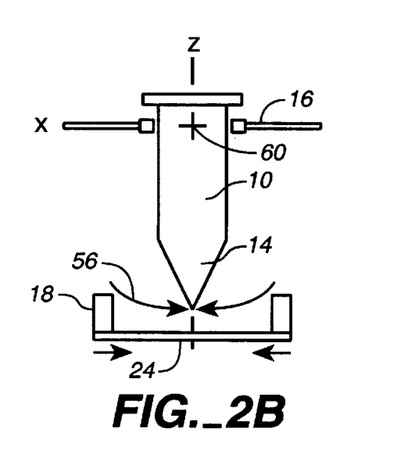

One way to mix and resuspend samples is "finger vortexing" (see FIG. 1). The action relies on a steadily held neck region of the tube while quickly, but gently, moving the bottom of the tube. The pull-and-release action moves the tube back to its original position. The action of finger vortexing is best described using a three dimensional model with a three axes, x-y-z, coordinate system (see FIG. 2). Herein described is an invention that simulates, upon multiple microsample tubes, this finger vortexing action.

2. Description of the Related Art

Biochemical and molecular techniques frequently require manipulations of samples with small volumes. These samples are often contained within microcentrifuge tubes, e.g., microliter volumes of chemical reactions at elevated temperatures (25–45° C.) or milliliter volumes of cell cultures incubated overnight for plasmid production. Apparatuses abound for handling small volumes, but mixing and incubating these samples are usually performed in large incubators or heated rooms within which are housed large circular shakers (onto which many researchers "lash" on or attach their microcentrifuge tube racks with tape or rubber bands). Smaller reciprocating shakers that can accommodate at least 24 microcentrifuge tubes are available but expensive. Heated models of the smaller reciprocating shakers are even more expensive.

These conventional products utilize the same rapid circular motion of the full-sized design, except in a miniaturized form. Due to the disproportionate increase in surface area to volume when converting from large flasks to microcentrifuge tube-sized samples, greater sheer forces will be produced along the walls of the tubes during high-speed circular motion, e.g., 2500 rpm. Unforeseen elements involved when using reciprocating technology potentially add unknown and complicating factors to the growth of microorganisms or reactions of chemicals contained in small volumes in vitro. As the trend for miniaturizing continues in biology, there is a greater demand for better and more efficient ways to mix small volume samples with a smoother and more size appropriate strategy.

One of the most efficient and simplest ways scientists are taught for mixing test-tube samples is the technique of finger vortexing the bottom of the tubes at regular intervals. When many microcentrifuge tubes require gentle and rhythmic thumping, a new design (with many more fingers) is necessary. This simple way of resuspending solutions in tubes eliminates the sheer forces produced, as in the aforementioned reciprocating shakers, which may damage vesicles or sheer-sensitive cells.

However, a recent technology search failed to uncover any microcentrifuge tube mixers which were based on the principle of finger vortexing. For example, U.S. Pat. No. 5,215,376 (Schulte et al.); U.S. Pat. No. 4,895,453 (Devlin et al.); U.S. Pat. No. 4,848,917 (Benin et al.); U.S. Pat. No. 4,747,693 (Kahl); U.S. Pat. No. 4,305,668 (Bilbrey); U.S. Pat. No. 4,118,801 (Kraft et al.); U.S. Pat. No. 4,057,148 (Meyer et al.); U.S. Pat. No. 4,004,883 (Meyer et al.); U.S. Pat. No. 3,850,580 (Moore et al.); and U.S. Pat. No. 3,401,034 (Moore) all describe mixers which use circular or orbital motion to swirl and mix tube contents. The orbital path is generated by an eccentric drive.

U.S. Pat. No. 3,159,384 (J. E. Davis, 1964) discloses an agitator which does not impart circular motion directly to the tubes. Instead, in conjunction with the unit's eccentric drive, a reciprocating agitation mechanism is incorporated "to break up particulate matter adhered to the walls of the tube of the flask."

Thus, none of the aforementioned patents directly or specifically addresses the issue of resuspending contents of microcentrifuge tubes based on the principle of finger vortexing.

The present invention is a multiple microcentrifuge tube mixer/incubator designed to accommodate small volume samples. The innovation lies in the low-intensity mechanism that pulls-and-releases of, for example, 1–1000 tubes at a time in a slow and rhythmic pattern. Thus, the present invention is an apparatus for mechanically finger vortexing micro-centrifuge tubes.

SUMMARY OF THE INVENTION

As stated above, the present invention discloses an apparatus for mechanically finger vortexing microcentrifuge tubes. The apparatus is comprised of a box having a bottom and four side walls; a tube-holding rack having a frame, where a top of a microcentrifuge tube is held in a pivotal position and where the rack is securely positioned within the box; a base plate having a plurality of upright ribs and, where the ribs cause a pull-and-release action either directly or indirectly on a microcentrifuge tube and where the base plate is reciprocately attached within the box; a wheel, where the wheel is connected to an armature and where the armature is connected to the base plate; and a motor with a shaft, where the shaft is connected to the wheel and where the motor is securely positioned within the box. In the operation of the apparatus, the motor and the shaft impart a circular motion to the wheel, and the armature transposes the circular motion of the wheel to a reciprocating motion on the base plate.

In addition, the box may be insulated and/or the box may have a hinged lid. The apparatus may also contain an internal heating element, a thermostat and/or an adjustable rheostat temperature switch. The apparatus may also contain a rheostat for regulating the speed of movement of the motor.

Furthermore, the wheel may contain a set screw for adjusting the distance between the rack and the base plate.

In a preferred embodiment, the apparatus also contains an internal heating element, a thermostat and/or an adjustable rheostat temperature switch, a rheostat to regulate speed of movement of the motor, an insulated box with a hinged lid and a set screw for adjusting the distance between the rack and the base plate.

The basic design of the invention has two accessories: a mechanism to pull-and-release either directly or indirectly the bottom of a microcentrifuge tube and a mechanism to secure the top or neck region of the tube in a pivotal position. Described in this patent are three examples of different embodiments of the invention.

Two embodiments of the invention use a reciprocating base plate with upright ribs to directly pull-and-release the tube bottoms. A third embodiment of the invention uses a reciprocating base plate with upright ribs to indirectly pull-and-release the tube bottoms.

For all three embodiments of the invention, the base plate is connected to a revolving wheel. The circular motion of the wheel is transposed to the back and forth motion of the base, i.e., this assembly runs along horizontal tracks. Over the ribs are vertically racked microcentrifuge tubes. The ribs, which move back and forth under the microcentrifuge tubes, resuspend the contents of the tubes by a pull-and-release motion either directly or indirectly on the tube bottoms.

The tube-holding rack is different in all three embodiments of the invention. In one embodiment, a rigid frame supports a sheet of elastic material which has holes bored out at, for example, one-inch spacing. Within this frame, a grid system separates each hole. Two major forces affect the action on the tube: the twisting of the elastic material at the sides of the tube and the stretching of the same flexible material at the front and back o the tube.

In another embodiment, a frame supports one or more sets of opposing, flexible prongs. The prongs hold each tube firmly and independently so that the tubes, once pulled, will move (release) uni-directionally back to their original positions. The recoil action of the tube subsequently mixes the tube contents, i.e., simulating the action of finger vortexing.

In another embodiment of the invention, a frame supports the tube-holding rack. The rack is made of rigid material and tilts width-wise on two rocker pins. A vertical pin attache d below the rack is pulled-and-released by the rib. A recoil mechanism acts on the vertical pin to quickly return the vertical pin (and rack) back to its original position. The tilting of the rack and its quick recoil action mix the tube contents in the same manner as finger vortexing.

BRIEF DESCRIPTION OF THE DRAWINGS

FIG. 1 shows th conventional finger vortexing method. A tube top 12 is held firmly between two fingers of one hand, for example, the thumb and forefinger. The tube bottom 14 is gently but firmly "thumped" by a finger of the other hand so that the tube 10 moves quickly and uni-directionally back to its original position. The recoil action of the tube, caused by the finger's pull-and-release of the tube bottom, mixes the tube contents.

FIG. 4A: the base plate 24 with attached rib 18 moves forward toward the tube bottom 14; the rib 18 comes into contact with the tube bottom 14.

FIG. 4B: the tube bottom 14 is pulled to the limit of the rib 18; the tube top 12 pivots on the y-axis 60.

FIG. 4C: the tube bottom 14 is released and returns to its original, vertical position; the rib 18 reaches extent of movement in a forward direction and stops.

FIG. 4D: the base plate 24 with attached rib 18 reverses direction and again comes into contact with the tube bottom 14.

FIG. 4E: the tube bottom 14 is pulled again to the limit of the rib 18; the tube top 12 pivots on the y-axis 60 in the opposite direction.

FIG. 4F: the tube bottom 14 is released and returns again to its original, vertical position; the rib 18 reaches extent of movement in a backward direction and stops.

FIGS. 5A–5C show a tube-holding rack utilizing a sheet or bands of elastic material.

FIG. 8A: the base plate 24 with attached rib 18 moves forward toward the vertical pin 72. The rib 18 comes into contact with the vertical pin 72.

FIG. 8B: the vertical pin 72 is pulled to the limit of the rib 18. The rack 20 pivots on the rocker pins 70.

FIG. 8C: the vertical pin 72 is released and the recoil mechanism 74 acts on the pin 72 to quickly return the pin 72 and rack 20 to its original, vertical position. The rib 18 reaches extent of movement in a forward direction and stops.

FIG. 8D: the base plate 24 with attached rib 18 reverses direction and again comes into contact with the vertical pin 72.

FIG. 8E: the vertical pin 72 is pulled again to the limit of the rib 18. The rack 20 pivots on the rocker pins 70 in the opposite direction.

FIG. 8F: the vertical pin 72 is released and the recoil mechanism 74 acts on the pin 72 to quickly return the pin 72 and rack 20 to its original, vertical position. The rib 18 reaches extent of movement in a backward direction and stops.

FIG. 9A shows the tube-holding rack 20 and subtending base assembly 24 attached to an existing shaker 76 in a cross-sectional view. The subtending base assembly 24 is attached to the moving base 78 of the existing shaker 76. The rack assembly 20 is attached to an outside frame 80 which is secured to the non-moving base 82 of the existing reciprocating or circular shaker 76.

FIG. 9B shows the tube-holding rack 20 and subtending base assembly 24 attached to an existing reciprocating or circular shaker 76 in a side view. The subtending base assembly 24 is secured to the moving base 78 of the existing shaker 76. The rack assembly 20 is attached to an outside frame 80 which is secured to the non-moving base 82 of the existing reciprocating or circular shaker 76.

a. 110 V AC plug (not shown) and electrical cord 36;
b. on/off switch-rheostat and knob 38 to regulate speed of movement or motor rpms;
c. 110 V AC motor 34 with turning shaft 42;
d. wheel 32 attached to motor shaft 42;
e. armature 28 attached eccentrically to revolving wheel 32 and sliding base plate 24 by connecting pins 30;
f. frame 22 supporting tube-holding rack 20 with opposing sets of prongs 16 to secure the tube tops 12;
h. insulated box 44 with bottom enclosure panel 46; and
i. hinged lid 48 to hold tubes 10 down in rack 20, i.e., to keep tubes 10 from shimmying-up out of prongs 16 during the thumping cycles.

a. 110 V AC plug (not shown) and electrical cord 36;
b. on/off switch-rheostat and knob 38 to regulate speed of movement or motor rpms;
c. 110 V AC motor 34 with turning shaft 42;
d. wheel 32 attached to motor shaft 42;
e. armature 28 attached eccentrically to revolving wheel 32 and sliding base plate 24 by connecting pins 30;
f. upright ribs 18 attached to the sliding base plate 24;
g. frame 22 supporting tube-holding rack 20 to secure the tube tops 12;
h. rocker pin 70 at each end of the tube-holding rack 20;
i. vertical pin 72 projecting downward at one end of the tube-holding rack 20;
j. recoil mechanism 74 which acts on the vertical pin 72 to quickly return the pin 72 to its resting, vertical position;
k. insulated box 44 with bottom enclosure panel 46; and
l. hinged lid 48 attached to the box 44 over the tube-holding rack 20.

DETAILED DESCRIPTION OF THE PREFERRED EMBODIMENT

The present invention discloses an apparatus or multiple minitube mixer for mechanically finger vortexing microcentrifuge tubes. The multiple minitube mixer is a device with an action incorporating the reciprocating motion of contemporary shaker mixers, except that in this application the reciprocating motion is responsible for the pull-and-release action of the tubes, where the tube tops are held in a pivotal position by a tube-holding rack.

The multiple microcentrifuge tube mixer/vortexer 40 herein described involves an apparatus consisting of the following features:

1. a frame 22 supporting a rack 20 with holes 64 drilled down the length of the rack 20 to hold a row of microcentrifuge tubes 10. The tube-holding rack 20 has two rocker pins 70, a vertical pin 72, and a recoil mechanism 74; all the tubes 10 are supported and contained within an insulated box 44 with a lid 48; and 2. a reciprocating table 24, with upright ribs 18, which is attached to a motor apparatus 34.

Figure 3:
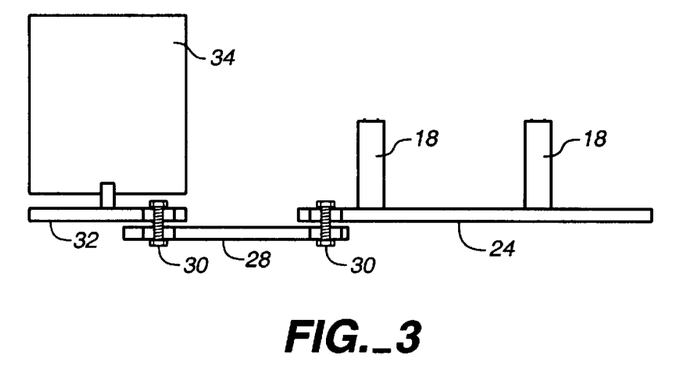
FIG. 3 shows reciprocating table 24 with attached ribs 18. The base 24 with attached ribs 18 is connected to a revolving wheel 32. The base in this example has a pin connection 30 to an armature 28 which has a pin connection 30 to a revolving wheel 32 and motor 34. The upright ribs on the base plate thus reciprocate with the revolving motion of the motor-wheel.
Figure 4A:
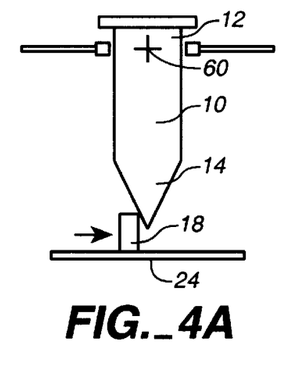
FIGS. 4A–4F show a sequence of events during a thumping cycle utilizing direct contact of the ribs to the tube bottoms. The ribs 18 move back and forth (solid arrow) to produce the thumping action of the tubes 10, as follows.
Figure 4B:
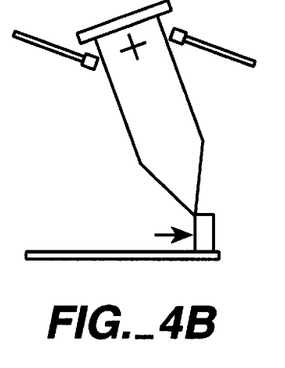
Figure 4C:
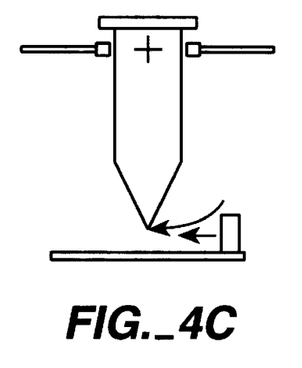
Figure 4D:
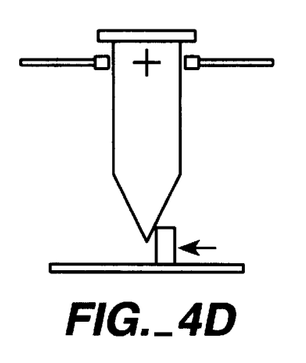
Figure 4E:
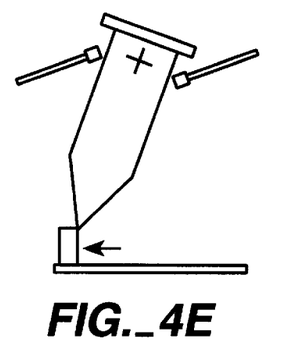
Figure 4F:
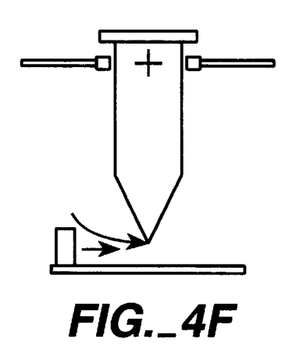
Figure 5A:
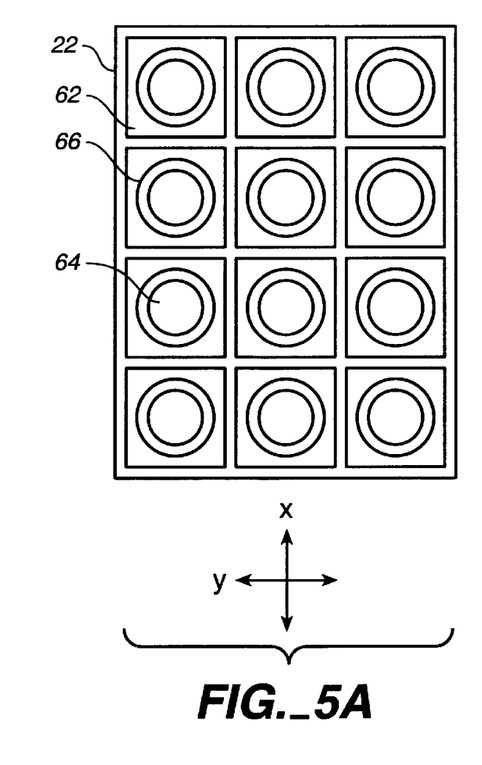
FIG. 5A shows an elastic sheet 62, e.g. rubber, with one-half inch holes 64 bored at one-inch spacing. A grommet 66 is placed in each hole 64 to firmly support a tube 10. A rigid frame 22 supports the rubber sheet 62 and separates each hole 64 and tube 10 from neighboring effects during the thumping cycle.
Figure 5B:
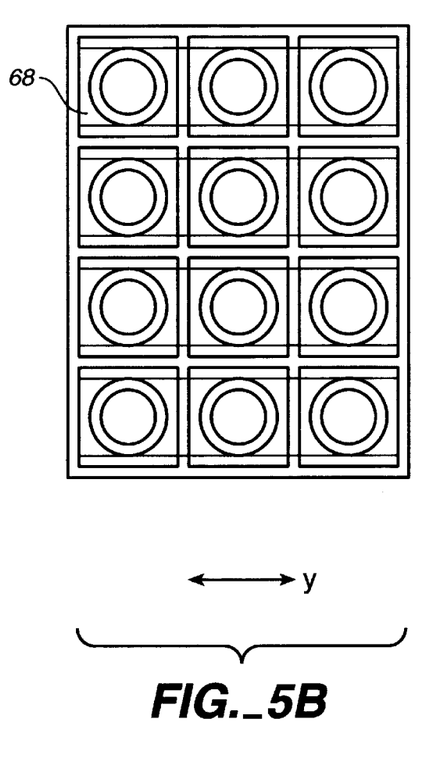
FIG. 5B shows the use of rubber bands 68 placed in the x-y plane 52 along the direction of the y-axis 60 (solid arrow). The stretch forces on the tube are primarily on the sides of the tube.
Figure 5C:
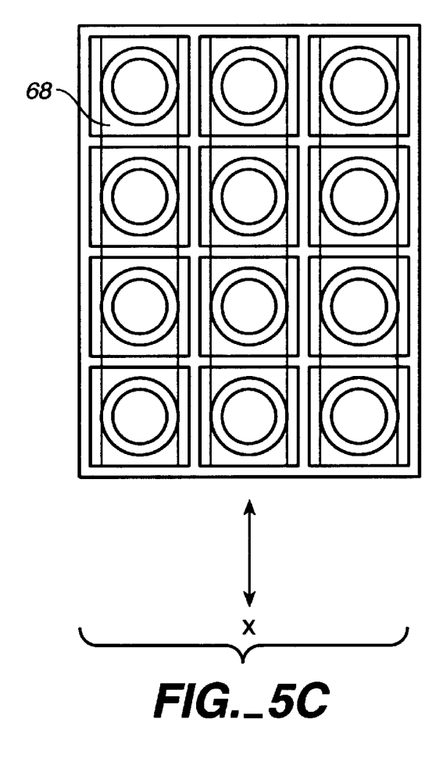
FIG. 5C shows the use of rubber bands 68 placed in the x-y plane 52 along the x-axis 58 (solid arrow). The stretch forces on the tube are primarily on the front and back of the tube.
Figure 6:
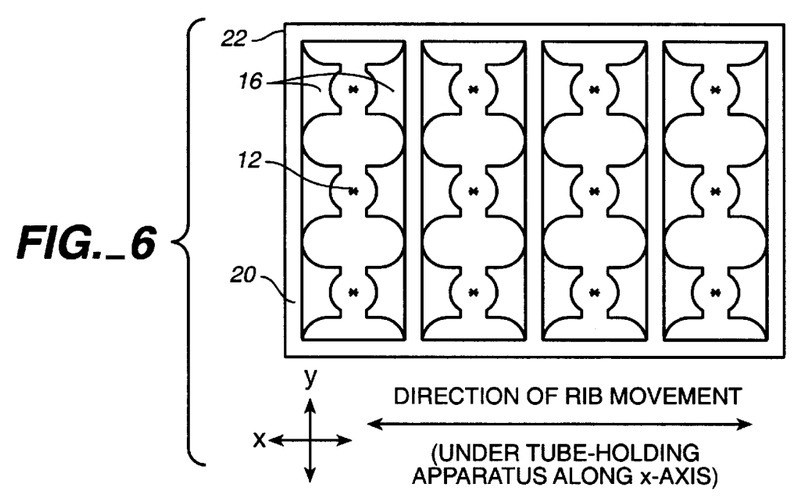
FIG. 6 shows a tube-holding rack 20 utilizing pairs of opposing, flexible prongs 16. The rack 20 is supported by a frame 22. The tube top 12 is held securely between the opposing prongs 16. The prongs restrict side-to-side motion of the tubes thus allowing for unidirectional movement of the tubes when the tube bottoms are pulled-and-released.

More specifically, a set of upright ribs 18 is mounted on a base plate 24. The base plate 24 is connected by a first pin 30 to an armature 28. The armature 28 is connected by a second pin 30 to a revolving wheel 32 (see FIG. 3). The circular motion of the wheel 32 is transposed by the armature 28 to the back and forth motion on the base plate 24 with attached ribs 18.

Over the ribs 18 are vertically racked microcentrifuge tubes 10. The ribs 18, which move back and forth under the microcentrifuge tubes 10, resuspend the contents of the tubes in a gentle and rhythmic motion (see FIG. 7).

Figure 7:
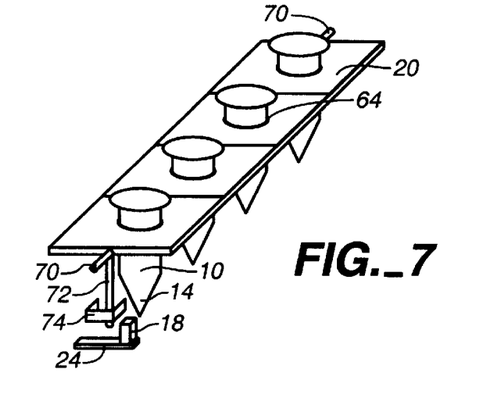
FIG. 7 shows a tube-holding rack 20 utilized as the pull-and-release mechanism. The rack 20 is shown in a side view. Holes 64 are drilled down the length of the rack 20, and microcentrifuge tubes 10 are placed in these holes 64. Two rocker pins 70 project outwardly from the ends of the rack 20. A vertical pin 72 projects downward; a recoil mechanism 74 acts on the pin 72 to quickly pull the vertical pin 72 back to its original position. The vertical pin 72 has direct contact with the rib 18.
Figure 8A:
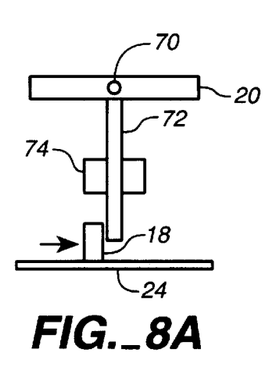
FIGS. 8A–8F show the sequence of events during a thumping cycle utilizing indirect contact of the ribs to the tube bottoms. The upright ribs 18 move back and forth (solid arrow) to produce the thumping action of the tubes 10 as follows.
Figure 8B:
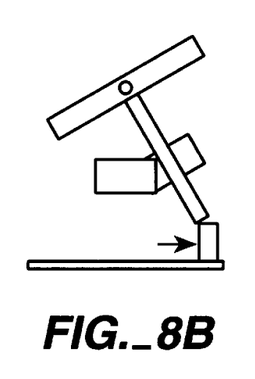
Figure 8C:
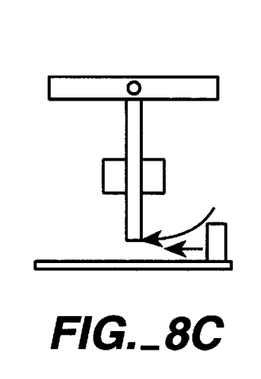
Figure 8D:
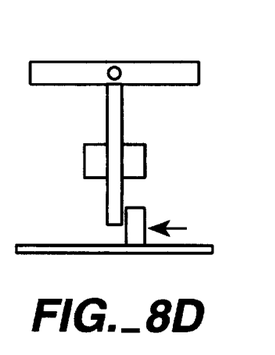
Figure 8E:
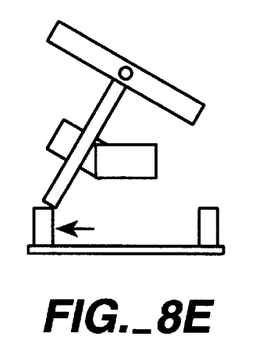
Figure 8F:
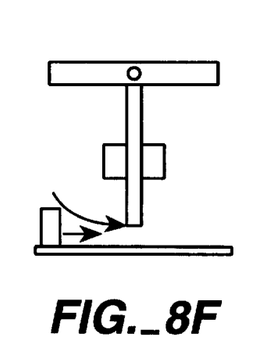
Figure 9A:
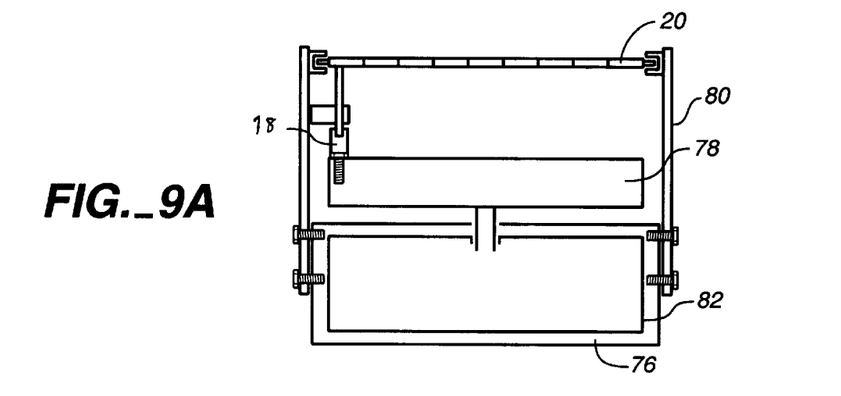
FIGS. 9A and 9B show a representation of possible attachments of the present invention for use on existing reciprocating or circular shakers.
Figure 9B:
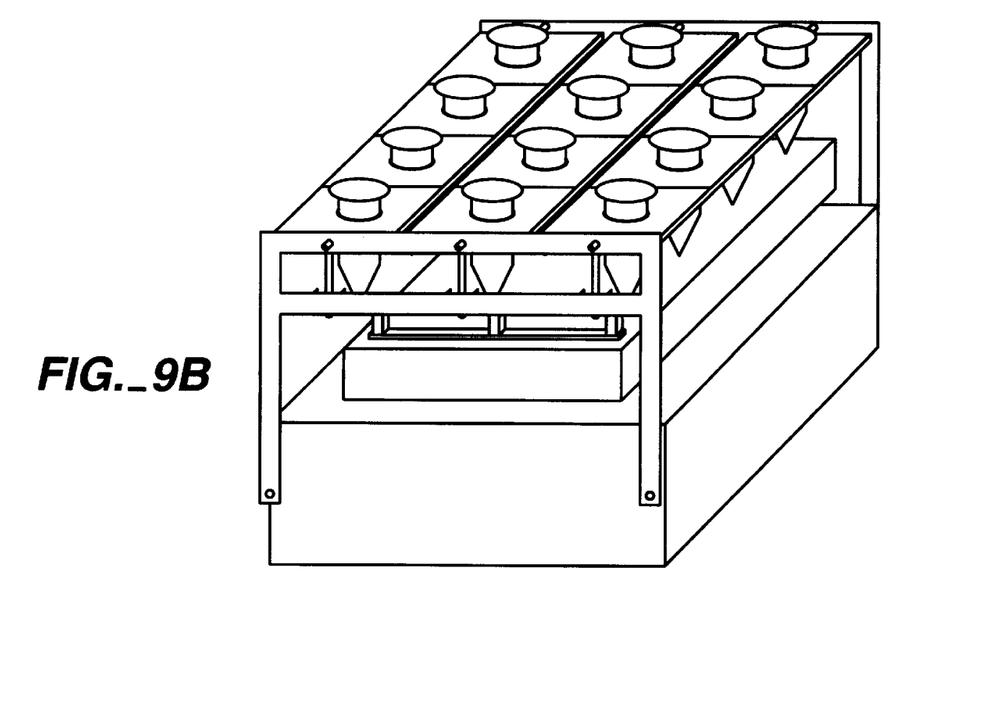
Figure 10:
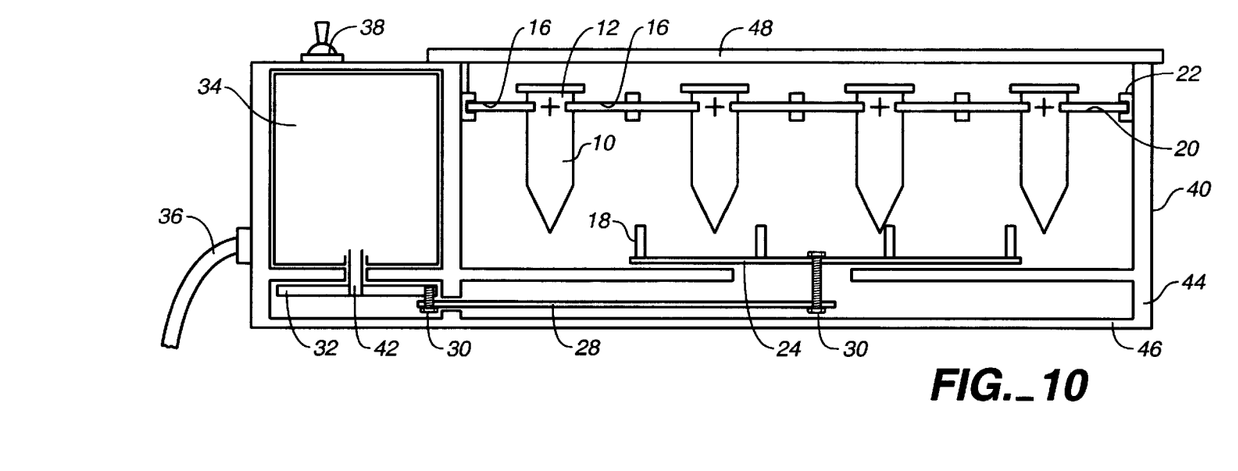
FIG. 10 shows one specific embodiment of the invention using direct contact of the tube bottoms with the ribs. The mixer 40 includes.

A rigid rack 20 with holes 64 drilled down the length of the rack 20 holds each tube 10 firmly and independently. The rack 20 tilts width-wise on two rocker pins 70, each of which are centrally located and outwardly projecting from the ends of the rack 20. At one end of the rack 20, a vertical pin 72 projects downward so that the pin 72 comes in contact with the base plate 24 with attached rib 18 instead of the tube bottoms 14.

The vertical pin 72 tilts, thus tilting the rack 20, as the rib 18 comes into contact with the pin 72 and pulls-and-releases the pin 72 (see FIGS. 8A–8F). A recoil mechanism 74 acts on the vertical pin 72 to quickly pull the pin 72 back to its original, resting position. The action of the pin 72 when it is pulled-and-released is felt by the whole row of tubes in the rack 20. Therefore any tube 10 in the rack 20 is indirectly pulled-and-released by the action of the base mechanism 24.

The finger vortexing action on the tube is caused by the pull-and-release of the rack's vertical pin and the recoil mechanism acting on the rack's vertical pin to quickly bring the pin back to its original position. This preferred embodiment of the present invention relieves the individual tube as the recipient of the pulling force, thereby eliminating any stress on the tube body. Instead of mixing individual tubes by direct contact on the tube bottom, a whole row of tubes can be effected indirectly by the action of a single extrinsic pin.

Figure 11:
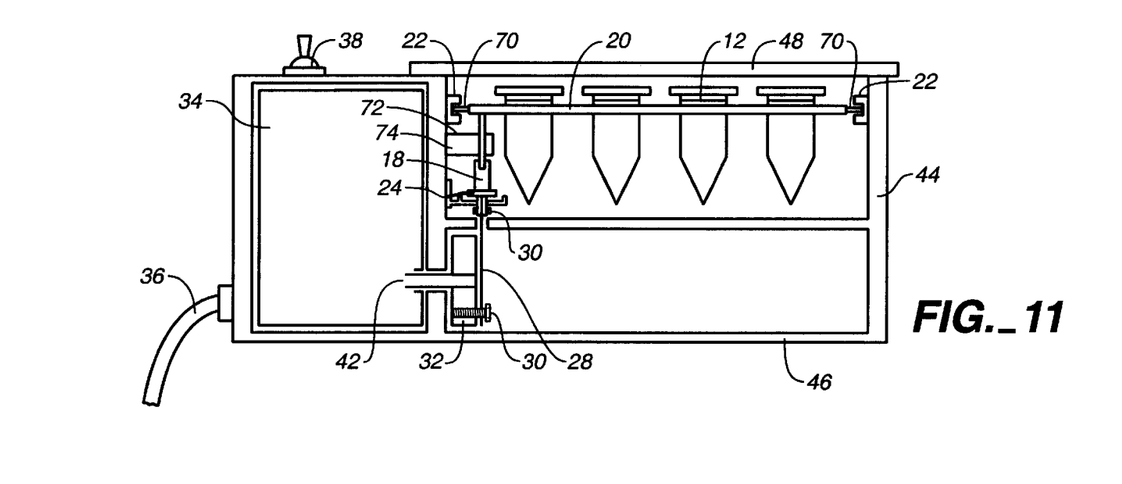
FIG. 11 shows one specific embodiment of the invention using indirect contact of the tube bottoms with the ribs. The mixer 40 includes.

A specific embodiment of the present invention is shown in FIG. 11. The micromixer 40 is comprised of the following:

1. 110 V AC plug (not shown) and electrical cord 36;
2. on/off switch-rheostat and knob 38 to regulate speed of movement or motor rpms;
3. 110 V AC motor 34 with turning shaft 42;
4. wheel 32 attached to motor shaft 42;
5. armature 28 attached eccentrically to revolving wheel 32 and sliding base plate 24 by connecting pins 30;
6. upright ribs 18 attached to the sliding base plate 24;
7. frame 22 to support tube-holding rack 20 to secure the tube tops 12;
8. rocker pins 70 at each end of the tube-holding rack 20;
9. vertical pin 72 projecting downward at one end of the tube-holding rack 20;
10. recoil mechanism 74 which acts on the vertical pin 72 to quickly return the pin 72 to its vertical position once displaced by the rib 18;
11. insulated box 44 with bottom enclosure panel 46; and
12. hinged lid 48 attached to the box 44 over the tube-holding rack 20.

The apparatus can be equipped with an internal heating element with, for example, thermal tape to maintain a pre-determined incubator temperature. A unit with a heating element, thermostat, and adjustable rheostat switch (to set temperature) is necessary for cultures or chemical reactions with specific temperature requirements. The device, with tube-holding rack removed and rib motion off, can be utilized as a microincubator for microplates, e.g., microtiter type, or one to eight 10 cm petri plates.

Although intended to be 110 V AC, a model could also be made available which has a wind-up coil good enough for overnight thumping, but also has no internal heat source.

Some of the advantages of the new invention over other available mixers are:

1. simplicity in design, i.e., the action simulates the gentle yet highly efficient action of finger vortexing;
2. the rapid, eccentrically-driven mechanism of contemporary shakers has been converted into a pull-and-release motion on the tubes;
3. greatly reduced sheer forces relative to the constant and forceful action experienced along the side walls of rapidly vortexed tubes in circular mini-shakers moving at high circular speeds, e.g., 500–2500 rpm;
4. less frictional heat produced than by the rapidly moving media along the sidewalls in microcentrifuge tubes under high circular velocities; and
5. better overall mixing of tube contents, i.e., the use of the tube's dished-bottom and side walls to thoroughly mix the tube contents.

The virtue of this design is its simplicity and low cost. The unit requires a low speed motor which moves the reciprocating ribs under a set of racked tubes. The invention itself is housed within an insulated box with a clear plastic lid and an optional heating element. By using contemporary components, the internal unit could be installed inexpensively. It is possible that a mini-shaker/incubator that gently homogenizes multiple samples in a small, incubated space could be offered for less than half the cost of the closest competition. The higher price of other contemporary devices has extremely limited access to alternative types of personal bench-top equipment. The price and the size differences would be revolutionary, especially in light of the audience that would be available to this device as a cost-effective means for molecular and chemical microanalyses.

This device will complement the array of bench-top equipment often identified with clinical and research and development molecular technologies. The invention's applicability is versatile—from elementary and high school biology classes to clinical and research facilities worldwide; the same technology could be offered in a wide variety of sizes and options, for example:

1. personal bench top/base classroom unit (e.g., 4×4 rack) and clinical/industrial/medical applications (e.g., 24×48 rack), and
2. simple accessory attachments for existing reciprocating shakers, e.g., attachable tube-holding rack and subtending rib assembly.

While the present invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. An apparatus for mechanically finger-vortexing microcentrifuge tubes, said apparatus comprising:
    a) a box having a bottom and four side wall;
    b) a tube-holding rack having a frame, wherein a top of a microcentrifuge tube is held in a pivotal position and wherein said rack is securely positioned within said box, said tube-holding rack comprising a sheet of elastic material with holes and grommets placed in said holes;
    c) a base plate having a plurality of upright ribs, wherein said ribs pull and release either directly or indirectly the bottom of a microcentrifuge tube and wherein said base plate is reciprocately attached within said box;
    d) a wheel, wherein said wheel is connected to an armature, wherein said armature is connected to said base plate; and
    e) a motor with a shaft, wherein said shaft is connected to said wheel and wherein said motor is securely positioned within said box; wherein said motor and said shaft impart a circular motion to said wheel and wherein said armature transposes said circular motion from said wheel to a reciprocating motion to said base plate.

2. The apparatus of claim 1, wherein said tube holding rack comprises rubber bands placed in an x-y plane along a y-axis of said tube-holding rack.

3. The apparatus of claim 1, wherein said tube-holding rack comprises rubber bands placed in an x-y plane along an x-axis of said tube-holding rack.

4. The apparatus of claim 1, wherein said box is insulated.

5. The apparatus of claim 1, wherein said box further comprises a hinged lid.

6. The apparatus of claim 1, further comprising an internal heating element.

7. The apparatus of claim 6, further comprising a thermostat.

8. The apparatus of claim 7, further comprising an adjustable rheostat temperature switch.

9. The apparatus of claim 8, wherein said box is insulated, wherein said box further comprises a hinged lid, and wherein said apparatus further comprises a rheostat to regulate speed of movement of said motor.

10. The apparatus of claim 1, wherein said apparatus further comprises a rheostat to regulate speed of movement of said motor.

11. An apparatus for mechanically finger vortexing microcentrifuge tubes, said apparatus comprising:
   a) a box having a bottom and four side walls;
   b) a tube-holding rack having a frame wherein a top of a microcentrifuge tube is held in a pivotal position, said tube-holding rack having two ends and having a rocker pin at each end and a vertical pin with a recoil mechanism at one end, wherein said tube-holding rack is securely positioned within said box;
   c) a base plate having a plurality of upright ribs, wherein said ribs contact said vertical pin attached to said tube-holding rack and wherein said base plate is reciprocately attached within said box;
   d) a wheel, wherein said wheel is connected to an armature, wherein said armature is connected to said base plate; and
   e) a motor with a shaft, wherein said shaft is connected to said wheel and wherein said motor is securely positioned within said box;
wherein said motor and said shaft impart a circular motion to said wheel and wherein said armature transposes said circular motion of said wheel to a reciprocating motion to said base plate.

12. An apparatus for mechanically finger-vortexing microcentrifuge tubes, said apparatus comprising:
   a) a box having a bottom and four side walls;
   b) a tube-holding rack having a frame and being securely positioned within the box, which rack holds a top of a microcentrifuge tube in a pivotal position and which microcentrifuge tubes have a freely moving bottom, allowing arcuate motion in an X-Z plane;
   c) a base plate which is reciprocately attached within said box and which has an upper surface;
   d) a plurality of upright ribs on the upper surface of said base plate, said ribs being configured to intermittently contact the bottoms of the microcentrifuge tubes, thereby pulling and releasing the bottoms of the microcentrifuge tubes as the base plate moves reciprocately within the box;
   e) a wheel connecting to an armature, which armature connects to the base plate; and
   f) a motor with a shaft, which shaft connects to the wheel;
   whereby the motor and the shaft impart a circular motion to the wheel and whereby the armature transposes the circular motion from the wheel to a reciprocating motion of the base plate.

13. An apparatus for mechanically finger-vortexing microcentrifuge tubes, said apparatus comprising:
   a) a box having a bottom and four side walls;
   b) a tube-holding rack having a frame comprised of rigid material, a top, a bottom and two ends, the top holding a plurality of a microcentrifuge tubes;
   c) a rocker pin attached to at least one end of the rack and a vertical pin attached to the bottom of the rack;
   c) a base plate which is reciprocately attaches within said box and which has an upper surface;
   d) at least one upright rib on the upper surface of said base plate, said rib being configured to intermittently pull the vertical pin to its limit causing the rack to pivot on the rocker pins, after which the rib releases the vertical pin;
   e) a recoil mechanism on the vertical pin, which recoil mechanism snaps the rack to its resting position after the rib releases the vertical pin.
   f) a wheel, which is connected to an armature, which in turn is connected to said base plate; and
   g) a motor with a shaft, which shaft is connected to the wheel;
wherein the motor and the shaft impart a circular motion to the wheel and wherein the armature transposes the circular motion from the wheel to a reciprocating motion to the base plate.

* * * * *